United States Patent [19]

van Helden et al.

[11] Patent Number: 4,497,966
[45] Date of Patent: Feb. 5, 1985

[54] PROCESS FOR THE PREPARATION OF NITROPHENYLALKANOLS

[75] Inventors: Robert van Helden; Petrus A. Kramer, both of Amsterdam, Netherlands

[73] Assignee: Shell Oil Company, Houston, Tex.

[21] Appl. No.: 529,910

[22] Filed: Sep. 7, 1983

[30] Foreign Application Priority Data

Sep. 14, 1982 [GB] United Kingdom ............... 8226198
Jul. 29, 1983 [EP] European Pat. Off. ........... 83201131

[51] Int. Cl.$^3$ .............................................. C07C 79/24
[52] U.S. Cl. .................................................. 568/705
[58] Field of Search .............................. 568/705, 704

[56] References Cited

U.S. PATENT DOCUMENTS 2,460,265  1/1949  Tindall ............................... 568/705
4,299,992 11/1981  Tungler et al. ..................... 568/587

FOREIGN PATENT DOCUMENTS 2327961  1/1975  Fed. Rep. of Germany ...... 568/705
3020236 12/1980  Fed. Rep. of Germany ...... 568/705
52-108941  9/1977  Japan ................................. 568/705
52-122330 10/1977  Japan ................................. 568/705
52-139035 11/1977  Japan ................................. 568/705
52-156825 12/1977  Japan ................................. 568/705
1201209  8/1970  United Kingdom ............... 568/705

OTHER PUBLICATIONS

Bakke, J., Acta Chem. Scand., 21 (7) (1967), pp. 1967-1978.

Primary Examiner—Werren B. Lone

[57] ABSTRACT

Nitrophenylalkanols are prepared by hydroxyalkylation of nitrotoluene(s) by the reaction with an aldehyde in the presence of a solid catalyst prepared by depositing an alkali metal compound on an alumina support.

8 Claims, No Drawings

PROCESS FOR THE PREPARATION OF NITROPHENYLALKANOLS

BACKGROUND OF THE INVENTION

1. Field of the Invention

This application relates to a process for the preparation of nitrophenylalkanols, and to the compounds thus prepared.

2. Description of the Prior Art

There exists an interest in the preparation of nitrophenylalkanols, since these compounds are useful intermediates in the production of other chemical compounds such as indole or 3-methylindole (cf. DT 2328330), herbicidal urea derivatives (cf. GB No. 8,218,455), or nitrostilbenes.

It is known to prepare the above-mentioned compounds by the addition of nitrotoluenes to aldehydes according to the following scheme:

$$RCH_3 + R'CHO \rightarrow RCH_2-CHOHR'$$

R represents herein a nitrophenyl group, which may be further substituted, and R'CHO represents an aliphatic or aromatic aldehyde, which aldehyde preferably does not have alphahydrogen atoms. By adding more aldehyde to the reaction mixture, further addition to yield nitrophenylalkanediols and/or -triols occurs. For the purpose of this application, alkanediols and alkanetriols are included in the broad class of alkanols. As catalyst a strong base like hydroxide or alkoxide dissolved in a polar, aprotic solvent has to be used [J. Bakke, Acta Chem. Scand. 21, 7 (1967) 1967–8]. The yields of this reaction are low, however, the more so because a Canizzaro-reaction of the aldehyde is competing. Similar reactions have been described in unexamined Japanese patent application Nos. 77.108941, 77.122330, 77.139035 and 77.156825 using various combinations of catalysts and solvents, in particular phase transfer catalysts, and in German Offenlegungsschrift No. 3020236, using special solvents and molar ratios of the reactants. Disadvantages of all these processes are the unsatisfactory yields and selectivities and/or the rather complicated working-up of the reaction products because homogeneous catalysts are used.

SUMMARY OF THE INVENTION

It is the object of the present invention therefore to provide an improved process for the preparation of nitrophenylalkanols comprising the hydroxyalkylation of nitrotoluene(s) by the reaction with an aldehyde.

According to the invention this is achieved by the employment of a special catalyst, in particular a solid catalyst based on alumina and containing alkali metal.

The invention thus relates to a process for the preparation of nitrophenylalkanols comprising the hydroxyalkylation of nitrotoluene(s) by the reaction with an aldehyde in the presence of a solid catalyst prepared by depositing an alkali metal compound on an alumina support.

Surprisingly this solid catalyst affords, with the desired products, a high yield and selectivity at moderate temperatures whereas after the reaction the catalyst can be separatead easily from the (liquid) reaction mixture, e.g. by filtration of the (solid) catalyst.

It should be noted that such catalysts are known per se, e.g. from British patent specification Nos. 1,458,129 and 1,439,692. These, however, relate to the aldol condensation of a certain aldehyde and an other carbonyl compound, and to the double bond isomerization of alkenes, respectively, which does not suggest that such catalysts would be active in the present hydroxyalkylation reaction.

The nitrotoluene used as starting material may be further substituted in the aromatic nucleus, in particular with chlorine, fluorine or an alkyl, alkoxy or a second nitro group. For example, the nitrotoluene can have the formula $RCH_3$ in which R is a nitrophenyl group optionally ring-substituted by chlorine, fluorine, a second nitro group or an alkyl or an alkoxy group containing from 1 to 6 carbon atoms. It appears that the best results are obtained with ortho- and paranitrotoluene(s); presumably, this is related with the ortho, para-directing effect of nitro groups. Preferably, O- and/or p-nitrotoluene(s) is (are) reacted with the aldehyde.

Although in special cases the reaction can be carried out with the reactants per se, the use of a solvent is preferred. Preferably, the reaction is carried out in an aprotic polar solvent. Suitable are dimethylformamide, tetrahydrofuran and dimethylsulphoxide, of which the latter is preferred.

It is a convenient aspect of the present invention that it usually suffices to mix the reactants and the catalyst into a solvent for the reaction to proceed: usually no heating is necessary. Suitably, the reaction is carried out at a temperature in the range of from about 0° C. to about 70° C., provided the reactants and the solvent form a liquid mixture at that temperature, of course. Very conveniently, the reaction is carried out at about 20°–25° C., i.e. room temperature. In order to speed up the reaction it is advisable to stir the reaction mixture or to agitate it in another way. The reaction time varies according to temperature, stirring rate, type of reactants and desired conversions, but generally reaction times of 1 to 100 hours, in particular of 4 to 24 hours, are employed.

The aldehyde used as the other reactant may be aliphatic, aromatic or hteroaromatic, e.g. formaldehyde, acetaldehyde, benzaldehyde, o-methoxybenzaldehyde, p-nitrobenzaldehyde or furfural. Of these the aldehydes having no alpha-hydrogen atoms are preferred, and particularly desirable is that the aldehyde has from 1 to 8 carbon atoms. (Para)formaldehyde is especially preferred.

The solid catalyst is prepared by depositing an alkali metal compound on an alumina support. It is not said, however, that the alkali metal will be present in the catalyst as the same compound; more likely, some chemical bond with the alumina carrier material will cause a complicated chemical structure. It probably is precisely this structure, which causes the specific catalytic properties.

As already stated, such catalysts are known per se, as from British patent specification Nos. 1,439,692 and 1,458,129, the disclosures of which are included herein by reference, and as illustrated below. For instance, particularly good results are obtained if the catalyst has been prepared by impregnating alumina with a solution containing an alkali metal carbonate or an alkali metal compound which is converted by heating into an alkali metal carbonate, followed by heating at a temperature at which the carbonate loses carbon dioxide. Though all aluminas are suitable, gamma-alumina is preferred.

The alkali metals have been found to increase the reaction rate considerably in the order $Li < Na < K$.

Preferred are, therefore, alkali metals having an atomic number of at least 19; these are potassium, rubidium and cesium. In view of its availability and price the alkali metal most preferred is potassium.

The alumina is preferably impregnated with an aqueous solution containing an alkali metal carbonate. Examples of alkali metal compounds which are converted by heating into an alkali metal carbonate are bicarbonates, alcoholates, chelates and carboxylates such as formates, acetates and oxalates. It is advantageous to impregnate the alumina with the calculated quantity of an aqueous solution corresponding to the pore volume. Subsequently, the water can be removed by drying at, say about 105°–125° C., upon which the impregnated alumina is heated at a temperature at which the carbonate loses carbon dioxide. This temperature depends on the alkali metal carbonate being used and is lowest for lithium carbonate. The preferred temperature range is about 160°–700° C., because supported lithium carbonate starts decomposing at about 160° C. and no further advantages are obtained at temperatures above about 700° C. Supported potassium carbonate starts decomposing at about 320° C. Accordingly, supported potassium, rubidium and cesium carbonate are preferably heated at a temperature between about 300° C. to about 650° C. and particularly between about 500° C. and about 600° C.

The heating of the alumina may be performed in the presence of an oxidizing or a non-oxidizing gas. As oxidizing gas air may be applied. As non-oxidizing gas nitrogen, noble gases, hydrogen and methane may be mentioned. Mixtures of two or more of the aforesaid non-oxidizing gases may be applied, for example of nitrogen and hydrogen.

Preference is given to gamma-aluminas having a specific surface area of more than about 100 m²/g. Suitable gamma-aluminas are commercially available in various forms, for instance as nibs, granules or powders. Particularly good results are obtained, for instance, with powders of 100 to 400 mesh, or granules with a diameter of 0.5 to 1.2 mm. Powders with pellet sizes of 15–35 mesh (1.3–0.5 mm) or 30–80 mesh (0.595–0.177 mm) may also be used. All the indicated mesh values are according to the U.S. Standard ASTM-E11-61. Prior to use the gamma-aluminas are usually heated at a temperature between about 500° C. to about 600° C. for some time.

The alkali metal compound has preferably been deposited in an amount equivalent to about 0.5–5 and particularly between 2.5 and 4 mmol alkali metal per gram of alumina, because the activity of the catalyst drops at alkali metal carbonate contents increasing above values equivalent to 5 mmol alkali metal per gram of alumina.

The catalyst may lose activity after some time of use and may then be regenerated by washing with a solvent, for example acetone or methanol, removing the solvent, for example at sub-atmospheric pressure and heating the dried catalyst at a temperature between, say, about 300° C. to about 650° C., for example 560° to 580° C.

The nitrophenylalkanol compound(s) may be isolated from the reaction mixture in any desired manner. For example, the catalyst is removed by centrifugation or filtration, whether or not with the aid of a filter aid. The product(s) is (are) obtained as a bottom product by distilling off solvent, unreacted aldehyde and unreacted nitrotoluene, suitably at sub-atmospheric pressure. It is recommended to keep the bottom temperature low in order to avoid dehydration of the nitrophenylalkanols.

The invention is further illustrated by the following examples

EXAMPLE I

Preparation of 2-(2-methyl-4-nitrophenyl)-1,3-propanediol 1.2 g (8.0 mmol) 4-Nitro-o-xylene and 0.66 g (22 mmol) paraformaldehyde were added to a mixture of 1.2 g catalyst in 4 ml of dimethylsulphoxide. The catalyst had been prepared by heating for 24 hours at 500° C. a composition containing 20 g $K_2CO_3$ per 100 g gamma-alumina, i.e. 2.89 mmol $K^+$/g $Al_2O_3$. The reaction mixture was stirred under nitrogen at 20°–25° C. The conversion of 4-nitro-o-xylene and the selectivity during the reaction were determined by gas-liquid chromatography, whereby the alcohols were analysed via their trimethylsilyl ethers. The results are given in Table I.

TABLE I

| Time (hours) | Conversion (%) | Selectivity (% w) | | |
|---|---|---|---|---|
| | | A | B | C |
| 9 | 78.4 | 4.4 | 7.2 | 88.4 |
| 24 | 85.6 | 5.3 | 5.4 | 89.3 |
| 96 | 96.4 | 6.3 | 2.8 | 90.9 |

A = 2-methyl-4-nitrostyrene
B = 2-(2-methyl-4-nitrophenyl)-ethanol
C = 2-(2-methyl-4-nitrophenyl)-1,3-propanediol

EXAMPLE II

Preparation of 2-(4-nitrophenyl)-1,3-propanediol and 2-methylol-2-(4-nitrophenyl)-1,3-propanediol To 0.6 g of the catalyst of Example I in 2.2 ml of dimethylsulphoxide were added 0.6 g p-nitrotoluene and 0.35 g paraformaldehyde. After stirring under nitrogen for 48 hours at 15°–20° C. the conversion of p-nitrotoluene amounted 71.6%. The reaction products were analysed by gas-liquid chromatography, whereby the alcohols again were first converted into their trimethylsilylethers. The results are given in Table II.

TABLE II

| | selectivity (% w) |
|---|---|
| 2-(4-nitrophenyl)-ethanol | 10.0 |
| 4-nitrostyrene | 1.8 |
| 2-(4-nitrophenyl)-1,3-propanediol | 46.7 |
| 2-(4-nitrophenyl)-1-propen-3-ol | 8.5 |
| 2-methylol-2-(4-nitrophenyl)-1,3-propanediol | 33.0 |

EXAMPLE III

Preparation of 2-(2-chloro-4-nitrophenyl)-1,3-propanediol

10 Grams of 2-chloro-4-nitrotoluene were dissolved in 25 ml of dimethylsulphoxide at 20° C., to which 3 grams of the catalyst of Example I and 4 grams of paraformaldehyde were added. This mixture was stirred under nitrogen at 20°–25° C. The conversion of 2-chloro-4-nitrotoluene amounted to 90%w after 7.5 hours, and to 100% after 24 hours, whereas the selectivity was 95%w in both cases (determined by gas-liquid chromatography as in the previous Examples). The reaction product was filtered to remove the catalyst and the latter was washed with dimethylsulphoxide (DMSO). The DMSO filtrate was distilled at 20 mm Hg in a film evaporator. The residue, consisting of 2-(2-chloro-4-nitrophenyl)-1,3-propanediol) (I) and DMSO, was diluted with water and extracted twice with ethyl acetate. After removal of the ethyl acetate 10.5 g of crude I was obtained. Recrystallization from toluene gave 8 g of I with the following NMR spectrum: (shift in ppm from TMS) 3.55 (m, 1H), 3.78 (dd, 4H), 4.73 (tr, 2—OH), 7.68 (d, 2H), 8.10 (dd, 2H), 8.20 (d, 1H).

What is claimed is:

1. A process for the preparation of nitrophenylalkanols comprising the hydroxyalkylation of nitrotoluene(s) by the reaction with an aldehyde containing from 1 to 8 carbon atoms in the presence of a solid catalyst prepared by impregnating alumina with a solution containing an alkali metal carbonate or an alkali metal compound which is converted by heating into an alkali metal carbonate, followed by heating at a temperature at which the carbonate loses carbon dioxide.

2. A process according to claim 1 wherein the nitrotoluene has the formula $RCH_3$ in which R is a nitrophenyl group optionally ring-substituted by chlorine, fluorine, a second nitro group or an alkyl or an alkoxy group containing from 1 to 6 carbon atoms.

3. A process according to claim 2 wherein o- or p-nitrotoluene or a mixture thereof is reacted with the aldehyde.

4. A process according to claim 2 wherein the reaction is carried out in an aprotic polar solvent.

5. A process according to claim 1 wherein the reaction is carried out at a temperature in the range of about 0° C. to about 70° C.

6. A process according to claim 4 wherein the alkali metal is potassium.

7. A process according to claim 6 wherein the alkali metal compound has been deposited in an amount equivalent to about 0.5–5 mmol alkali metal per gram of alumina.

8. A process according to claim 7 wherein the aldehyde is (para)formaldehyde, acetaldehyde, benzaldehyde, o-methoxybenzaldehyde, p-nitrobenzaldehyde or furfural.

* * * * *